US009839733B2

(12) United States Patent
Reichenbach et al.

(10) Patent No.: US 9,839,733 B2
(45) Date of Patent: Dec. 12, 2017

(54) APPARATUS AND METHOD FOR MODIFYING PRESSURE-FLOW CHARACTERISTICS OF A PUMP

(71) Applicant: Thoratec Corporation, Pleasanton, CA (US)

(72) Inventors: Steven H. Reichenbach, Pleasanton, CA (US); Yu Fai Law, Daly City, CA (US)

(73) Assignee: TC1 LLC, St. Paul, MN (US)

( * ) Notice: Subject to any disclaimer, the term of this patent is extended or adjusted under 35 U.S.C. 154(b) by 80 days.

(21) Appl. No.: 14/746,527

(22) Filed: Jun. 22, 2015

(65) Prior Publication Data

US 2015/0283312 A1  Oct. 8, 2015

Related U.S. Application Data

(63) Continuation of application No. 13/166,680, filed on Jun. 22, 2011, now Pat. No. 9,089,635.

(Continued)

(51) Int. Cl.
*A61M 1/10* (2006.01)
*A61M 1/12* (2006.01)

(52) U.S. Cl.
CPC ............ *A61M 1/1086* (2013.01); *A61M 1/10* (2013.01); *A61M 1/101* (2013.01); *A61M 1/1001* (2014.02);
(Continued)

(58) Field of Classification Search
CPC .................................................. A61M 1/1086
See application file for complete search history.

(56) References Cited

U.S. PATENT DOCUMENTS

| 4,957,504 A | 9/1990 | Chardack |
| 5,112,202 A | 5/1992 | Oshima et al. |

(Continued)

FOREIGN PATENT DOCUMENTS

| CA | 2237203 | 3/1998 |
| EP | 1354606 | 10/2003 |

(Continued)

OTHER PUBLICATIONS

U.S. Appl. No. 13/166,680 , "Final Office Action", dated Nov. 20, 2014, 10 pages.

(Continued)

*Primary Examiner* — Thomas J Sweet
*Assistant Examiner* — Cheryl Miller
(74) *Attorney, Agent, or Firm* — Kilpatrick, Townsend & Stockton, LLP

(57) ABSTRACT

Blood pump systems including a continuous flow blood pump and methods for controlling a continuous flow blood pump operate the blood pump to simulate target pressure-flow characteristics that are different from native pressure-flow characteristics of the blood pump. A method for controlling a continuous flow blood pump driven by a motor includes operating the motor at a first rotational rate. A first flow rate of the continuous flow blood pump driven at the first rotational rate is measured and/or estimated. The first flow rate is used to determine a second rotational rate based on target pump characteristic data corresponding to target pressure-flow characteristics for the continuous flow blood pump different from pressure-flow characteristics of the continuous flow blood pump when driven by the motor at a constant rotational speed. The second rotational rate is different from the first rotational rate. The motor is then operated at the second rotational rate.

20 Claims, 8 Drawing Sheets

Related U.S. Application Data

(60) Provisional application No. 61/357,440, filed on Jun. 22, 2010.

(52) U.S. Cl.
CPC ..... *A61M 1/122* (2014.02); *A61M 2205/3334* (2013.01)

(56) References Cited

U.S. PATENT DOCUMENTS

| | | | |
|---|---|---|---|
| 5,171,212 | A | 12/1992 | Buck et al. |
| 5,211,546 | A | 5/1993 | Isaacson et al. |
| 5,220,259 | A | 6/1993 | Werner et al. |
| 5,289,821 | A | 3/1994 | Swartz |
| 5,352,180 | A | 10/1994 | Candelon et al. |
| 5,362,206 | A | 11/1994 | Montgomery et al. |
| 5,370,509 | A | 12/1994 | Golding et al. |
| 5,613,935 | A | 3/1997 | Jarvik |
| 5,695,471 | A | 12/1997 | Wampler |
| 5,711,753 | A | 1/1998 | Pacella et al. |
| 5,725,357 | A | 3/1998 | Nakazeki et al. |
| 5,840,070 | A | 11/1998 | Wampler |
| 5,888,242 | A | 3/1999 | Antaki et al. |
| 5,947,703 | A | 9/1999 | Akamatsu et al. |
| 6,015,434 | A | 1/2000 | Yamane |
| 6,027,498 | A | 2/2000 | Mutch et al. |
| 6,066,086 | A | 5/2000 | Antaki et al. |
| 6,068,588 | A | 5/2000 | Goldowsky |
| 6,071,093 | A | 6/2000 | Hart |
| 6,074,180 | A | 6/2000 | Khanwilkar et al. |
| 6,080,133 | A | 6/2000 | Wampler |
| 6,100,618 | A | 8/2000 | Schoeb et al. |
| 6,120,537 | A | 9/2000 | Wampler |
| 6,129,660 | A | 10/2000 | Akamatsu et al. |
| 6,132,363 | A | 10/2000 | Freed et al. |
| 6,135,943 | A | 10/2000 | Yu et al. |
| 6,142,752 | A | 11/2000 | Akamatsu et al. |
| 6,146,325 | A | 11/2000 | Lewis et al. |
| 6,158,984 | A | 12/2000 | Cao et al. |
| 6,162,167 | A | 12/2000 | Goldstein et al. |
| 6,176,822 | B1 | 1/2001 | Nix et al. |
| 6,183,412 | B1 | 2/2001 | Benkowski et al. |
| 6,217,541 | B1 | 4/2001 | Yu et al. |
| 6,227,797 | B1 | 5/2001 | Watterson et al. |
| 6,234,772 | B1 | 5/2001 | Lancisi et al. |
| 6,234,998 | B1 | 5/2001 | Wampler et al. |
| 6,250,880 | B1 | 6/2001 | Woodard et al. |
| 6,264,635 | B1 | 7/2001 | Wampler et al. |
| 6,277,078 | B1 | 8/2001 | Porat et al. |
| 6,295,877 | B1 | 10/2001 | Aboul-Hosn et al. |
| 6,302,661 | B1 | 10/2001 | Khanwilkar et al. |
| 6,368,083 | B1 | 4/2002 | Wampler et al. |
| 6,394,769 | B1 | 5/2002 | Bearnson et al. |
| 6,395,026 | B1 | 5/2002 | Aboul-Hosn et al. |
| 6,422,990 | B1 | 7/2002 | Prem |
| 6,443,983 | B1 | 9/2002 | Nagyszalanczy et al. |
| 6,447,441 | B1 | 9/2002 | Yu et al. |
| 6,458,164 | B1 | 10/2002 | Weiss |
| 6,468,041 | B2 | 10/2002 | Ozaki |
| 6,532,964 | B2 | 3/2003 | Aboul-Hosn et al. |
| 6,547,530 | B2 | 4/2003 | Ozaki et al. |
| 6,572,530 | B1 | 6/2003 | Araki et al. |
| 6,575,717 | B2 | 6/2003 | Ozaki et al. |
| 6,589,030 | B2 | 7/2003 | Ozaki |
| 6,605,032 | B2 | 8/2003 | Benkowski et al. |
| 6,623,420 | B2 | 9/2003 | Reich et al. |
| 6,626,644 | B2 | 9/2003 | Ozaki |
| 6,634,224 | B1 | 10/2003 | Schöb et al. |
| 6,640,617 | B2 | 11/2003 | Schöb et al. |
| 6,688,861 | B2 | 2/2004 | Wampler et al. |
| 6,707,200 | B2 | 3/2004 | Carroll et al. |
| 6,709,240 | B1 | 3/2004 | Schmalz et al. |
| 6,709,382 | B1 | 3/2004 | Horner |
| 6,711,943 | B1 | 3/2004 | Schöb et al. |
| 6,716,189 | B1 | 4/2004 | Jarvik et al. |
| 6,783,328 | B2 | 8/2004 | Lucke et al. |
| 6,808,482 | B1 | 10/2004 | Pacella et al. |
| 6,817,836 | B2 | 11/2004 | Nose et al. |
| 6,866,625 | B1 | 3/2005 | Ayre et al. |
| 6,949,066 | B2 | 9/2005 | Bearnson et al. |
| 6,966,748 | B2 | 11/2005 | Woodard et al. |
| 6,991,595 | B2 | 1/2006 | Burke et al. |
| 7,010,954 | B2 | 3/2006 | Siess et al. |
| 7,138,776 | B1 | 11/2006 | Gauthier et al. |
| 7,141,943 | B2 | 11/2006 | Song et al. |
| 7,150,711 | B2 | 12/2006 | Nüsser et al. |
| 7,156,873 | B2 | 1/2007 | Nose et al. |
| 7,160,242 | B2 | 1/2007 | Yanai |
| 7,160,243 | B2 | 1/2007 | Medvedev et al. |
| 7,175,588 | B2 | 2/2007 | Morello |
| 7,229,474 | B2 | 6/2007 | Hoffmann et al. |
| 7,239,098 | B2 | 7/2007 | Masino |
| 7,284,956 | B2 | 10/2007 | Nose et al. |
| 7,396,327 | B2 | 7/2008 | Morello |
| 7,435,059 | B2 | 10/2008 | Smith et al. |
| 7,462,019 | B1 | 12/2008 | Allarie et al. |
| 7,494,459 | B2 | 2/2009 | Anstadt et al. |
| 7,497,116 | B2 | 3/2009 | Miyakoshi et al. |
| 7,511,443 | B2 | 3/2009 | Townsend et al. |
| 7,591,777 | B2 | 9/2009 | LaRose et al. |
| 7,645,225 | B2 | 1/2010 | Medvedev et al. |
| 7,699,588 | B2 | 4/2010 | Mendler |
| 7,748,964 | B2 | 7/2010 | Suzuki et al. |
| 7,850,594 | B2 | 12/2010 | Sutton et al. |
| 7,854,631 | B2 | 12/2010 | Townsendl et al. |
| 7,861,582 | B2 | 1/2011 | Miyakoshi et al. |
| 7,887,479 | B2 | 2/2011 | LaRose et al. |
| 7,951,062 | B2 * | 5/2011 | Morello ............ A61M 1/1086 600/17 |
| 7,976,271 | B2 | 7/2011 | LaRose et al. |
| 8,157,720 | B2 | 4/2012 | Marseille et al. |
| 8,303,482 | B2 | 11/2012 | Schima et al. |
| 8,382,830 | B2 | 2/2013 | Maher et al. |
| 8,506,470 | B2 | 8/2013 | LaRose et al. |
| 8,517,699 | B2 | 8/2013 | Horvath |
| 8,556,795 | B2 | 10/2013 | Bolyard et al. |
| 8,597,350 | B2 | 12/2013 | Rudser et al. |
| 8,764,621 | B2 | 7/2014 | Badstibner et al. |
| 8,870,739 | B2 | 10/2014 | LaRose et al. |
| 8,882,477 | B2 | 11/2014 | Fritz, IV et al. |
| 8,956,275 | B2 | 2/2015 | Bolyard et al. |
| 9,089,635 | B2 | 7/2015 | Reichenbach et al. |
| 2001/0009645 | A1 | 7/2001 | Noda et al. |
| 2002/0183628 | A1 | 12/2002 | Reich et al. |
| 2003/0139643 | A1 | 7/2003 | Smith et al. |
| 2004/0047736 | A1 * | 3/2004 | Nose ................ A61M 1/101 417/44.1 |
| 2004/0084398 | A1 | 5/2004 | Breitschwerdt et al. |
| 2004/0084399 | A1 | 5/2004 | Cook et al. |
| 2004/0152944 | A1 | 8/2004 | Medvedev et al. |
| 2004/0234397 | A1 | 11/2004 | Wampler et al. |
| 2005/0025630 | A1 | 2/2005 | Ayre et al. |
| 2005/0071001 | A1 | 3/2005 | Jarvik |
| 2005/0107657 | A1 | 5/2005 | Carrier et al. |
| 2005/0159639 | A1 | 7/2005 | Skliar et al. |
| 2005/0208095 | A1 | 9/2005 | Hunter et al. |
| 2006/0149331 | A1 | 7/2006 | Mann et al. |
| 2006/0241335 | A1 | 10/2006 | Benkowski et al. |
| 2007/0073393 | A1 | 3/2007 | Kung et al. |
| 2007/0142923 | A1 | 6/2007 | Ayre et al. |
| 2007/0231135 | A1 | 10/2007 | Wampler et al. |
| 2007/0282298 | A1 | 12/2007 | Mason et al. |
| 2008/0080983 | A1 | 4/2008 | Wampler et al. |
| 2008/0085184 | A1 | 4/2008 | Wampler et al. |
| 2008/0089779 | A1 | 4/2008 | Wampler et al. |
| 2008/0089797 | A1 | 4/2008 | Wampler et al. |
| 2008/0183287 | A1 | 7/2008 | Ayre et al. |
| 2008/0281146 | A1 | 11/2008 | Morello |
| 2009/0005632 | A1 | 1/2009 | Schima et al. |
| 2009/0099406 | A1 | 4/2009 | Salmonsen et al. |
| 2009/0138080 | A1 | 5/2009 | Siess et al. |
| 2009/0156885 | A1 | 6/2009 | Morello et al. |
| 2010/0087742 | A1 | 4/2010 | Bishop et al. |
| 2010/0130809 | A1 | 5/2010 | Morello et al. |

(56) References Cited

U.S. PATENT DOCUMENTS

| | | |
|---|---|---|
| 2010/0152526 A1 | 6/2010 | Pacella et al. |
| 2010/0166570 A1 | 7/2010 | Hampton et al. |
| 2010/0168848 A1 | 7/2010 | Horvath et al. |
| 2010/0185280 A1 | 7/2010 | Ayre et al. |
| 2010/0222632 A1 | 9/2010 | Poirier |
| 2010/0222633 A1 | 9/2010 | Poirier |
| 2010/0222634 A1 | 9/2010 | Poirier |
| 2010/0222635 A1 | 9/2010 | Poirier |
| 2010/0222878 A1 | 9/2010 | Poirier et al. |
| 2010/0241223 A1 | 9/2010 | Lee et al. |
| 2010/0327687 A1 | 12/2010 | Iannello et al. |
| 2011/0071337 A1 | 3/2011 | Thompson et al. |
| 2011/0098807 A1 | 4/2011 | Frazier et al. |
| 2011/0237863 A1 | 9/2011 | Ricci et al. |
| 2011/0313237 A1 | 12/2011 | Miyakoshi et al. |
| 2011/0313517 A1 | 12/2011 | Reichenbach et al. |
| 2011/0318203 A1 | 12/2011 | Ozaki et al. |
| 2012/0078031 A1 | 3/2012 | Burke et al. |
| 2012/0226097 A1 | 9/2012 | Smith et al. |
| 2012/0245681 A1 | 9/2012 | Casas et al. |
| 2013/0331934 A1 | 12/2013 | Kabir et al. |
| 2014/0100413 A1 | 4/2014 | Casas et al. |
| 2014/0194985 A1 | 7/2014 | Vadala, Jr. |
| 2014/0275723 A1 | 9/2014 | Fritz, IV et al. |
| 2014/0275727 A1 | 9/2014 | Bonde et al. |
| 2014/0303426 A1 | 10/2014 | Kerkhoffs et al. |
| 2014/0357937 A1 | 12/2014 | Reyes et al. |
| 2015/0051438 A1 | 2/2015 | Taskin |

FOREIGN PATENT DOCUMENTS

| | | |
|---|---|---|
| JP | 2002224066 | 8/2002 |
| JP | 2004278375 | 10/2004 |
| WO | 9729795 | 8/1997 |
| WO | 0105023 | 1/2001 |
| WO | 0112070 | 2/2001 |
| WO | 03015609 | 2/2003 |
| WO | 2004028593 | 4/2004 |
| WO | 2009051593 | 4/2009 |
| WO | 2010101107 | 9/2010 |

OTHER PUBLICATIONS

U.S. Appl. No. 13/166,680, "Non-Final Office Action", dated Jan. 17, 2014, 8 pages.

U.S. Appl. No. 13/166,680, "Notice of Allowance", dated Mar. 16, 2015, 10 pages.

U.S. Appl. No. 13/166,680, "Supplemental Notice of Allowance", dated Jun. 18, 2015, 4 pages.

AU2011270999, "First Examiner Report", dated Jun. 16, 2015, 4 pages.

Ayre et al., "Identifying physiologically significant pumping states in implantable rotary blood pumps using non-invasive system observers", IEEE Engineering in Medicine and Biology Society, vol. 1, 2003, pp. 439-442.

Barletta et al., "Design of a bearingless blood pump", Proceedings from Third International Symposium on Magnetic Suspension Technology, 1995, pp. 265-274.

EP11729848.9, "Office Action", dated Apr. 21, 2015, 5 pages.

PCT/US2011/041449, "International Search Report and Written Opinion", dated Oct. 7, 2011, 11 pages.

Yamazaki et al., "Development of a miniature intraventricular axial flow blood pump", Journal of American Society for Artificial Internal Organs, vol. 39, No. 3, 1993, pp. M224-M230.

\* cited by examiner

Modifying pressure-flow characteristics of a continuous flow pump (e.g., an axial flow pump) to simulate a particular set of pressure-flow characteristics (e.g., a centrifugal flow pump)

estimating a flow rate of the continuous flow pump from the speed of an electric motor and from the current or power consumption of the electric motor, wherein the electric motor drives the continuous flow pump

adjusting the speed of the electric motor as a function of an estimated flow rate of the pump (e.g., the axial flow pump) and a set speed of the electric motor to simulate the desired pressure-flow characteristics (e.g., the centrifugal flow pump), wherein the function can be derived from the pressure-flow characteristics of the pump (e.g., the axial flow pump) and the desired pressure-flow characteristics (e.g., the centrifugal flow pump)

FIG. 7

APPARATUS AND METHOD FOR MODIFYING PRESSURE-FLOW CHARACTERISTICS OF A PUMP

CROSS-REFERENCES TO RELATED APPLICATIONS

This application is a continuation of U.S. application Ser. No. 13/166,680 filed Jun. 22, 2011, entitled "APPARATUS AND METHOD FOR MODIFYING PRESSURE-FLOW CHARACTERISTICS OF A PUMP," which application claims the benefit of U.S. Provisional Application No. 61/357,440, filed Jun. 22, 2010, the contents of which are hereby incorporated in their entirety by reference.

FIELD OF THE INVENTION

The present invention relates to a ventricular assist device and a method for modifying the characteristics of the hydrodynamic pump of a ventricular assist device, in particular to a method for modifying the pressure-flow characteristics of the hydrodynamic pump of a ventricular assist device. The present invention further relates to a computer readable storage medium wherein such an invention is stored.

BACKGROUND

The human heart is a pump—a complex and critical pump. The heart can become damaged or dysfunctional over time. When wear and damage to the heart become sufficiently serious, the heart fails to pump and circulate blood normally, resulting in a condition known as heart failure. Around the world millions of people suffer from heart failure. Many people are unresponsive to pharmacological intervention and could benefit from a heart transplant. Since there is a shortage of donor hearts, blood pumps of different forms, including implantable ones, have gradually evolved into a viable treatment option.

In a diseased state, one or both ventricles of a patient's heart can become weakened to an extent that mechanical intervention to supplement circulation is needed to keep the patient alive. In extreme circumstances, the entire heart is removed and replaced with an artificial heart while in other cases a device that assists the heart is used. A blood pump system used to assist the heart without removing the natural heart is commonly referred to as a ventricular assist device.

Although either of the ventricles of the heart may function in a weakened state, failure of the left ventricle is more common. Normally, blood enters the left ventricle through the mitral valve and, during heart systole, the blood is ejected through the aortic valve and into the aorta by the squeezing action of the left ventricle. To assist a failing left ventricle, a ventricular assist device can be attached to the apex of the left ventricle supplementing blood flow between the left ventricle and the aorta. As a result, blood entering the left ventricle may either be ejected through the aortic valve by the ventricle or pass through the ventricular assist device into the aorta.

Ventricular assistance has been performed by a variety of blood pump designs. The majority of the early ventricular assist devices, such as positive displacement pumps, pumped blood in a pulsatile manner. In this case, the ventricular assist device allows an internal sac to passively fill with blood, and then utilizes pneumatic action to compress the internal sac, ejecting the blood into the patient's aorta to supplement circulation.

These pulsatile ventricular assist devices are large and can only be used as an implantable treatment option for patients with a large body surface area.

To overcome the size and complexity problems associated with the pulsatile ventricular assist devices, designers have begun to use continuous flow pumps. These pumps are smaller than their pulsatile counterparts and are more reliable. Continuous flow or rotary pumps are normally either centrifugal flow pumps or axial flow pumps. In the centrifugal flow pumps, the rotors are shaped to accelerate the blood circumferentially and thereby cause it to move toward the outer rim of the pump, whereas in the axial flow pumps the rotors are cylindrical with helical blades, causing the blood to be transported in the direction of the rotor's rotational axis. Alternative designs exist spanning these two general types and are termed diagonal or mixed flow pumps. A main advantage of axial flow pumps over centrifugal flow pumps is that they are smaller for a given fluid displacement capacity.

BRIEF SUMMARY

A pump delivers fluid from a low pressure inlet to a higher pressure outlet. The performance of the pump can be characterized by the relationship among the pump's flow rate, pressure differential and rotor speed. The flow rate is measured in terms of volume per unit time. The pressure differential, which is the difference between the pump's outlet pressure and inlet pressure, can be measured in terms of force per unit area, such as "pounds per square inch" or "PSI." The pressure differential can also be measured in terms of pressure head—a term used to represent the internal energy of the fluid due to the fluid pressure. The pressure head is measured in terms of a height of a liquid, such as "millimeters of mercury" or "inches of water."

One way to mathematically describe the characteristics of a pump is to express the pressure differential or head across the pump as a function of the flow rate of the pump. This function can be represented as a curve with the pressure differential as the Y axis and the flow rate as the X axis. This function or curve is affected by the pump speed. In other words, the characteristics of a pump can be described by a family of pressure differential versus flow rate functions or curves, each of which corresponds to a pump speed.

At a given pump speed, the pressure differential of a pump decreases as the flow rate increases, or, put differently, the flow rate of the pump decreases as the pressure differential increases. This implies that, as the pressure differential of the pump increases, it is more difficult for the pump to generate fluid flow, resulting in a lower flow rate.

The pressure or head differential and flow rate (H-Q) relationship of a pump depends on the pump type and the specifics of pump design. For example, the axial flow pumps and the centrifugal flow pumps tend to have different characteristics. In comparison, for a given speed, the pressure differential of an axial flow pump tends to have less effect on the flow rate of the pump. In other words, as the pressure differential decreases, the flow rate of an axial flow pump increases less than the flow rate of a centrifugal flow pump.

The H-Q relationship of a pump of a ventricular assist device directly influences how the ventricular assist device responds to changes in physiological conditions, such as changes in physiologic pressures. Clinically it has been suggested that some aspects of the H-Q relationship of a centrifugal flow pump is advantageous due to the increased sensitivity of the pump's flow rate to the pump's differential pressure. To address this difference of the axial flow pump while maintaining its advantages, the inventors of the present application have invented a simple, inexpensive method for modifying the H-Q characteristics of a continuous flow pump to simulate different H-Q characteristics such as more desirable H-Q characteristics. As a result, a ventricular assist device having an axial flow pump that is modified according to the present invention has not only the small size and high flow rate associated with a conventional axial flow pump but also the desirable H-Q characteristics of a centrifugal flow pump. In general, this method can be used to modify any pump to achieve any desired H-Q characteristics.

The following is a description of certain aspects and embodiments of the present invention.

A first embodiment is directed to a method for controlling a blood pump driven by a motor. The method includes the step of modifying operational pressure-flow characteristics of the blood pump to simulate target pressure-flow characteristics different from native pressure-flow characteristics of the blood pump, including making an adjustment to the speed of the motor, and the adjustment made according to a function of the flow rate of the blood pump, of pressure differential across the blood pump, or of power consumption of the motor.

In an aspect according to the first embodiment, the method includes estimating the flow rate of the blood pump from an initial speed of the motor and from the current or power consumption of the motor, and using the estimated flow rate to determine a target speed of the motor.

In an aspect according to the first embodiment, the method comprising measuring the flow rate of the blood pump, and using the measured flow rate to determine a target speed of the motor.

In an aspect according to the first embodiment, the function for adjusting the speed is derived from the native pressure-flow characteristics of the blood pump and the target pressure-flow characteristics.

In an aspect according to the first embodiment, the step of modifying the operational pressure-flow characteristics of the pump includes estimating a pressure differential across the blood pump from the speed of the motor and from the current or power consumption of the motor.

In an aspect according to the first embodiment, the step of modifying the operational pressure-flow characteristics of the blood pump includes measuring the pressure across the blood pump.

In an aspect according to the first embodiment, the blood pump is an axial flow pump and the target pressure-flow characteristics are pressure-flow characteristics of a centrifugal flow pump.

In an aspect according to the first embodiment, the step of modifying the operational pressure-flow characteristics of the blood pump includes controlling the blood pump to operate on a specified power-speed relation.

A second embodiment is directed to a controller configured for controlling a pump driven by an electric motor. The controller includes a control system that is programmed to make a modification to the operational pressure-flow characteristics of the pump to simulate target pressure-flow characteristics different from native pressure flow characteristics of the pump. The control system is programmed to make the modification with an adjustment to the speed of the electric motor, and the adjustment is made according to a function of the flow rate of the pump, of the pressure differential across the pump, or of power consumption of the electric motor.

In an aspect according to the second embodiment, the control system is programmed to make the modification by estimating the flow rate of the pump from the initial speed of the motor and from the current or power consumption of the electric motor, and to use the estimated flow rate to determine a target speed of the electric motor.

In an aspect according to the second embodiment, the function for adjusting the speed is based on the native pressure-flow characteristics of the pump and the target pressure-flow characteristics.

In an aspect according to the second embodiment, the control system is programmed to make the modification by estimating a pressure differential across the pump from the speed of the electric motor and from the current or power consumption of the electric motor.

In an aspect according to the second embodiment, the control system is programmed to make the modification by measuring the pressure across the pump.

In an aspect according to the second embodiment, the pump is an axial flow pump and the target pressure-flow characteristics are pressure-flow characteristics of a centrifugal flow pump.

In an aspect according to the second embodiment, the control system is programmed to make the modification by controlling the pump to operate on a specified power-speed relation.

A third embodiment is directed to a method for controlling a blood pump driven by a motor. The method includes modifying operational pressure-flow characteristics of the blood pump to simulate a target pressure-flow curve different from native pressure-flow curves of the blood pump, including repeatedly making adjustments to the speed of the motor. For each adjustment to the speed of the motor, the motor changes speed from an initial speed to a target speed such that the operating point of the pump on a graph of pressure differential versus flow rate moves from an initial point to a target point. The initial point and the target point have the same flow rate value and different pressure differential values. All the target points lie on the same target pressure-flow curve.

In an aspect according to the third embodiment, the method includes, for each adjustment to the speed of the motor, estimating or measuring the flow rate value, and determining the target speed of the motor from the flow rate value and the initial speed of the motor.

In an aspect according to the third embodiment, the method includes, for each adjustment to the speed of the motor, determining the target speed from a function derived from the native pressure pressure-flow curves of the blood pump and the target pressure-flow curve.

A fourth embodiment is directed to a pump system functioning as a ventricular assist device. The pump system includes a pump driven by the electric motor, and a control system that is programmed to modify operational pressure-flow characteristics of the pump to simulate target pressure-flow characteristics different from native pressure-flow characteristics of the pump. The control system is programmed to make the modification with an adjustment to the speed of the electric motor, and the adjustment is made according to a function of the flow rate of the pump, of the pressure differential across the pump, or of power consumption of the motor.

In an aspect according to the fourth embodiment, the control system is programmed to make the modification by estimating the flow rate of the pump from the initial speed of the motor and from the current or power consumption of the electric motor, and to use the estimated flow rate to determine a target speed of the electric motor.

In an aspect according to the fourth embodiment, the function for adjusting the speed is derived from the native pressure-flow characteristics of the pump and the target pressure-flow characteristics.

In an aspect according to the fourth embodiment, the control system is programmed to make the modification by estimating a pressure differential across the pump from the speed of the electric motor and from the current or power consumption of the electric motor.

In an aspect according to the fourth embodiment, the control system is programmed to make the modification by measuring the pressure across the pump.

In an aspect according to the fourth embodiment, the control system is programmed to make the modification by controlling the pump to operate on a specified power-speed relation.

A fifth embodiment is directed to a method of controlling a blood pump driven by a motor. The method includes modifying operational pressure-flow characteristics of the blood pump to make the flow rate of the blood pump more responsive to changes in the pressure differential of the blood pump, including making an adjustment to the speed of the motor from an initial speed to a target speed. The adjustment is made according to a function of the flow rate of the blood pump or of power consumption of the motor.

In an aspect according to the fifth embodiment, the method includes estimating the flow rate of the blood pump from the initial speed of the motor and from the current or power consumption of the motor, and using the estimated flow rate to determine the target speed of the motor.

In an aspect according to the fifth embodiment, the function is derived from the native pressure-flow characteristics of the blood pump and pressure-flow characteristics of a centrifugal flow pump.

In an aspect according to the fifth embodiment, the step of modifying the operational pressure flow characteristics of the blood pump includes estimating a pressure differential across the blood pump from the speed of the motor and from the current or power consumption of the motor.

In an aspect according to the fifth embodiment, the step of modifying the operational pressure flow characteristics of the blood pump includes measuring the pressure across the blood pump.

In an aspect according to the fifth embodiment, the step of modifying the operational pressure flow characteristics of the blood pump includes controlling the blood pump to operate on a specified power-speed relation.

A sixth embodiment is directed to a computer-readable storage medium, with instructions thereon that are executable by a computer to modify operational pressure-flow characteristics of a blood pump driven by a motor to simulate target pressure-flow characteristics different from the native pressure-flow characteristics of the blood pump, by an adjustment to the speed of a motor from an initial speed to a target speed, the adjustment being made according to a function of the flow rate of the blood pump or of power consumption of the motor.

In an aspect according to the sixth embodiment, instructions to modify the operational pressure-flow characteristics of the blood pump include instructions to measure the flow rate of the blood pump, or estimate the flow rate of the blood pump from the speed of the motor and from the current or power consumption of the motor.

In an aspect according to the sixth embodiment, the function for making the adjust is derived from the native pressure-flow characteristics of the blood pump and the target pressure-flow characteristics.

In an aspect according to the sixth embodiment, instructions to modify the operational pressure-flow characteristics of the blood pump include instructions to measuring the pressure across the blood pump, or to estimate a pressure differential across the blood pump from the speed of the motor and from the current or power consumption of the motor.

In an aspect according to the sixth embodiment, instructions to modify the operational pressure-flow characteristics of the blood pump include instructions to control the blood pump to operate on a specified power-speed relation.

BRIEF DESCRIPTION OF THE DRAWINGS

FIG. 7 is a flow chart showing computer instructions for carrying out the step of an exemplary method of the invention.

DETAILED DESCRIPTION OF THE INVENTION

Figure 1:
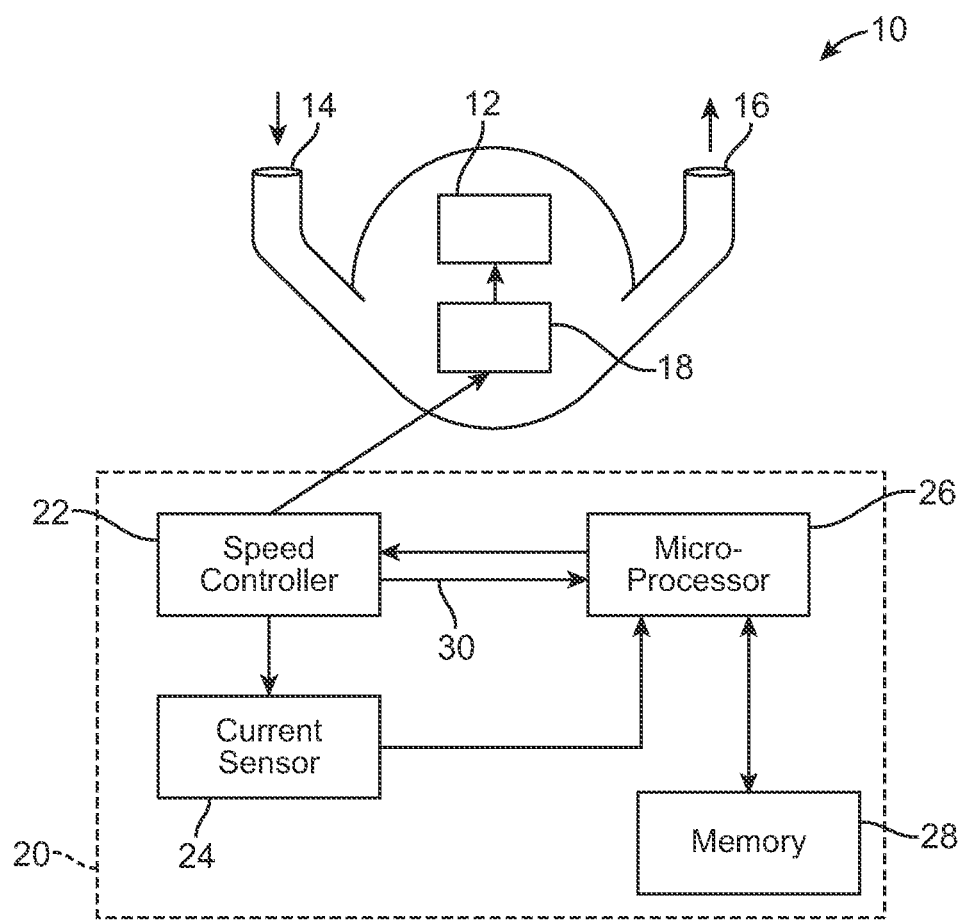
FIG. 1 is a schematic drawing of a ventricular assist device according to the present invention.

FIG. 1 shows a schematic diagram of a ventricular assist device 10 according to one embodiment of the present invention. The device 10 includes an implantable blood pump (e.g., a continuous flow pump) 12 in fluid communication with a patient's circulatory system. The blood pump 12 has an inlet 14 and an outlet 16. The inlet 14 may connect to a conduit (not shown) that may in turn connect to a patient's circulatory system, such as at the left ventricle of the patient's heart. The outlet 16 may connect to another conduit (not shown) that may in turn connect to the patient's circulatory system downstream of the first conduit, such as in the aorta. The continuous flow pump 12 can be implanted in the patient's abdomen, chest cavity, or in another location proximate to the heart. Since an implantable blood pump (e.g., an axial blood pump) is well known, the blood pump 12 will not be described in further detail. For exemplary purpose, the blood pump 12 is described herein as a continuous, axial flow pump, but one with ordinary skill in the art can appreciate that the teachings in this disclosure apply generally to modifying the pressure-flow characteristics of any continuous flow pump and not merely one in an axial flow configuration. In other words, the teachings in this disclosure can be applied to a continuous, axial flow pump or a continuous, centrifugal pump to simulate a desired pressure-flow characteristic.

The ventricular assist device 10 also includes an electric motor 18 for driving the axial flow pump 12. The electric motor 18 can be of any suitable type. For example, the electric motor 18 can be an alternating current electric motor or a direct current electric motor. The electric motor 18 could be a continuous type electric motor or a step type electric motor. The electric motor 18 and axial flow pump 12 may form an integral unit or separate units.

The ventricular assist device 10 also includes a control system 20 that can be located inside or outside the blood pump 12. The control system 20 can be configured to operate the blood pump 12 (or the electric motor 18) at a particular speed or speeds to provide adequate assistance to the patient's heart. The control system 20 can change the speed of the electric motor 18 by supplying a varying voltage from a speed controller 22 of the control system 20 through a control line.

The control system 20 can include a microprocessor 26 that is used to establish and control an appropriate set point for the pump 12. The control system 20 can also include a current sensor 24 that detects the current drawn by the electric motor 18, and the microprocessor 26 can be used to compute the flow rate of the pump 12 using that current signal. The microprocessor 26 can compute the motor load (or the pump's power 20 consumption) from the current signal. In addition, the microprocessor 26 can send or receive a signal via a speed line (e.g., communication from speed controller to microprocessor) 30 that indicates the rotational speed of the electric motor 18 (or the pump 12). The speed of the electric motor 18 (or the pump 12) can be measured from the electric motor's back electromotive force signal. The control system 20 can further include memory 28 for storing data.

In one embodiment, the control system controls the speed of a continuous flow blood pump in a way that modifies the pressure-flow characteristics of the continuous flow blood pump for at least one of two purposes: (1) to simulate a particular pressure-flow relationship or characteristic (e.g., that of a centrifugal flow pump) or (2) to make the flow rate of the axial flow pump more responsive to physiological responses reflected in the changes to the pressure differential of blood pump. As further explained below, the pressure-flow relationship is modified in accordance to a particular target pressure-flow relationship (i.e., an individual curve on a pressure-flow graph), traversing many different relationships in a pressure-flow graph, where each relationship is defined by the hydraulic design of the pump at different motor speed.

Thus, one of the goals of this the target pressure-flow relationship is intended to simulate increased responsiveness to physiological responses. This target pressure-flow relationship is generally represented by at least one continuous curve that is characteristic of a pump type different from the pump in which it is being implemented such that the pump will operate along the entire range of at least this one curve. This target pressure-flow relationship is not a representation of physiological changes such as blood viscosity change or change in peripheral vascular resistance, not intended to limit operation of the blood pump in a defined area in the pressure-flow graph set by a pressure range and a flow range, and not intended to target a specific physiological phenomenon such as adjusting the speed of the pump temporarily to prevent back flow of blood into ventricles.

Rather, the objective is to change the fundamental operational pressure-flow characteristic of a pump different from its native characteristic.

A method, by which the control system controls the pump speed to modify the pressure-flow characteristics of the continuous flow pump, is described as follows.

The performance of the continuous flow pump can be characterized by the relationship among the pump's pressure differential H, flow rate Q, and rotor speed S.

Figure 2:
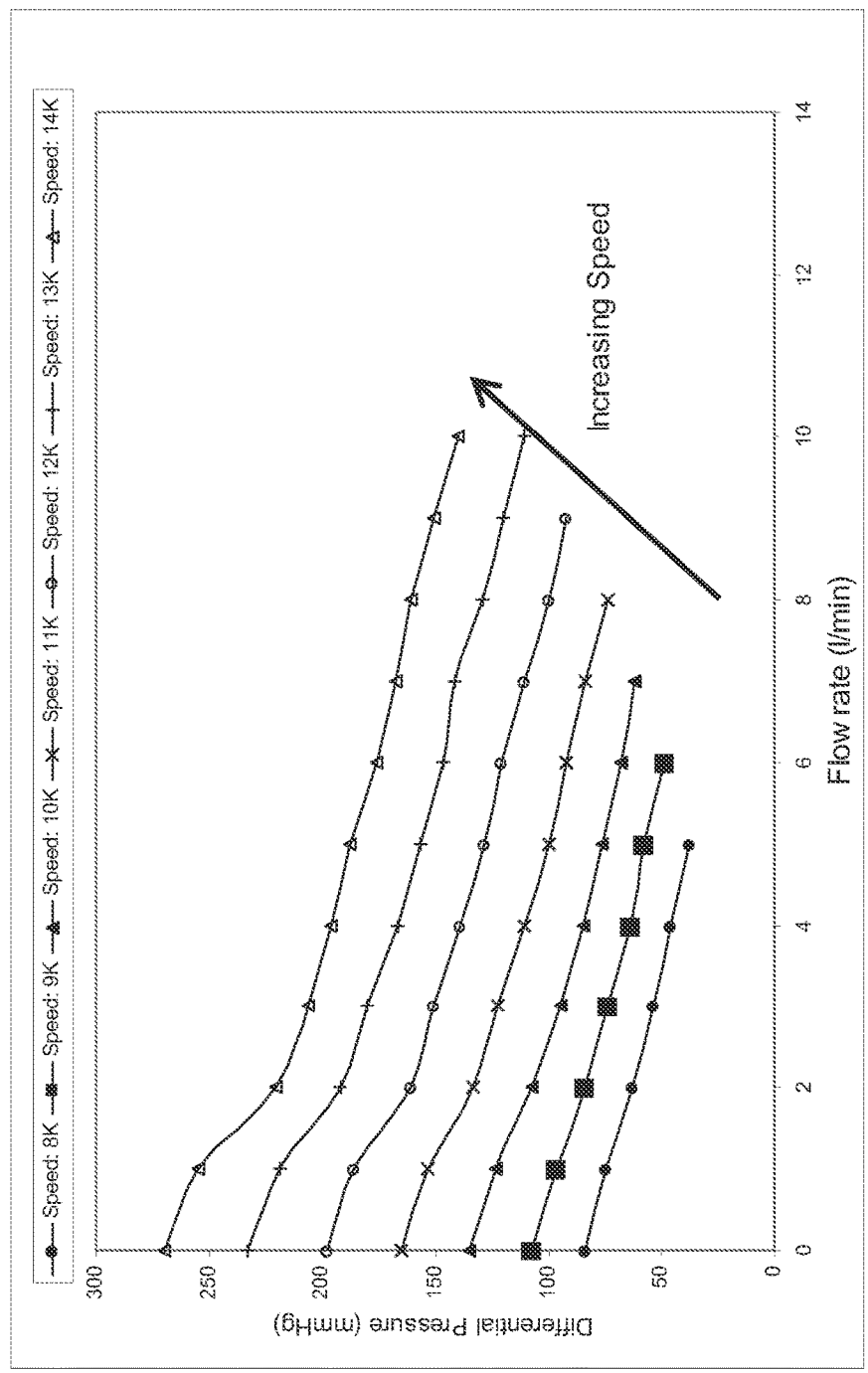
FIG. 2 is a chart illustrating the characteristics of an axial flow pump of a ventricular assist device.

This relationship can be represented by a map or graph, as shown in FIG. 2. In FIG. 2, the pressure differential H is represented by the Y axis and the flow rate Q by the X axis. For a given pump speed, the relationship between the pressure differential H and the flow rate Q is represented by an H-Q curve on the graph. As a result, a map of the continuous flow pump includes a family of H-Q curves, each curve representing a relationship between the pressure differential H and the flow rate Q for every different pump speeds.

The family of H-Q curves in FIG. 2 represents the native H-Q characteristics of the pump. The native H-Q characteristics, including the shape, steepness (slope) and location of individual H-Q curves, is unique to the particular hydraulic design of pump and can vary from one type of pump to another.

As used herein "H-Q" is an abbreviation for "pressure-flow." The phrases "H-Q curve" and "pressure-flow curve" have the same meaning and are used interchangeably. The phrases "H-Q characteristics" and "pressure-flow characteristics" have the same meaning and are used interchangeably.

In following descriptions of "modifying" H-Q characteristics of a pump, it is to be understood that the native H-Q characteristics of the pump are not modified. What is being modified is the operational H-Q characteristics of the pump. In prior art, the relationship between pressure differential H and flow rate Q during operation of a pump corresponds to the native H-Q characteristics of the pump. In the present invention, a pump is controlled such that the relationship between H and Q corresponds to the native H-Q characteristics of another pump or other target H-Q characteristics that differ from the native H-Q characteristics of the pump being controlled. That is, the pump is controlled to have operational H-Q characteristics that match native H-Q characteristics of another pump or other target H-Q characteristics that differ from the native H-Q characteristics of the pump being controlled.

The map of an axial flow pump, as shown in FIG. 2, can be generated by test data. The term "map" refers to mapping or relationships between pressure differential H, flow rate Q and rotor speeds which are native to the pump. To obtain test data, for example, the flow rate of the pump can be recorded for different values of pump pressure differential and pump speed. Specifically, the value of the pump pressure differential can be increased from a minimum value to a maximum value by a given increment, and the value of the pump speed can be increased from a minimum value to a maximum value by a given increment for each value of the pump pressure differential. The flow rate can be recorded for each combination of pressure differential and pump speed values. This process produces the test data used to generate the map of the axial flow pump.

A way to represent the native relationship among the pump's pressure differential H, flow rate Q, and rotor speed S is by means of a mathematical formula or function $f_{AF}$ with the pressure differential H as the dependent variable and the flow rate Q and rotor speed S as the independent variables:

$$H = f_{AF}(Q, S) \qquad (1)$$

The subscript "AF" indicates that function $f_{AF}$ is for an axial flow pump. In general, $f_{AF}$ can be for any blood pump being controlled to simulate H-Q characteristics that differ from the native H-Q characteristics of the pump. The function $f_{AF}$ may be derived from the test data used to generate the pump map shown in FIG. 2. For example, function $f_{AF}$ can use a polynomial of any desirable degree to interpolate or approximate, optionally based on test data, the H-Q curve for each pump speed. As a result, function $f_{AF}$ is composed of a set of polynomials that represent the H-Q curves of the pump map, where each polynomial corresponds to a value of pump speed.

Alternatively, function $f_{AF}$ can use spline interpolation to represent the test data. For example, function $f_{AF}$ can use a piecewise polynomial to interpolate the H-Q curve for each pump speed. As a result, function $f_{AF}$ is composed of a set of piecewise polynomials that represent the H-Q curves of the pump map, where each piecewise polynomial corresponds to a value of pump speed.

Similarly, a function $f_C$ can also be used to represent the native relationship among a centrifugal flow pump's pressure differential H, flow rate Q, and rotor speed S:

$$H=f_C(Q,S) \tag{2}$$

This function $f_C$ can be obtained from the test data of a centrifugal flow pump in a manner similar to how function $f_{AF}$ is obtained from the test data of the axial flow pump. The subscript "C" indicates that function $f_C$ can be for a centrifugal flow pump. In general, this function $f_C$ can be used to represent any desired pump characteristics, not just the characteristics of a centrifugal flow pump. For example, function $f_C$ may simply represent the characteristics of a pump that has the desired flow rate sensitivity to pressure differential.

Figure 3:
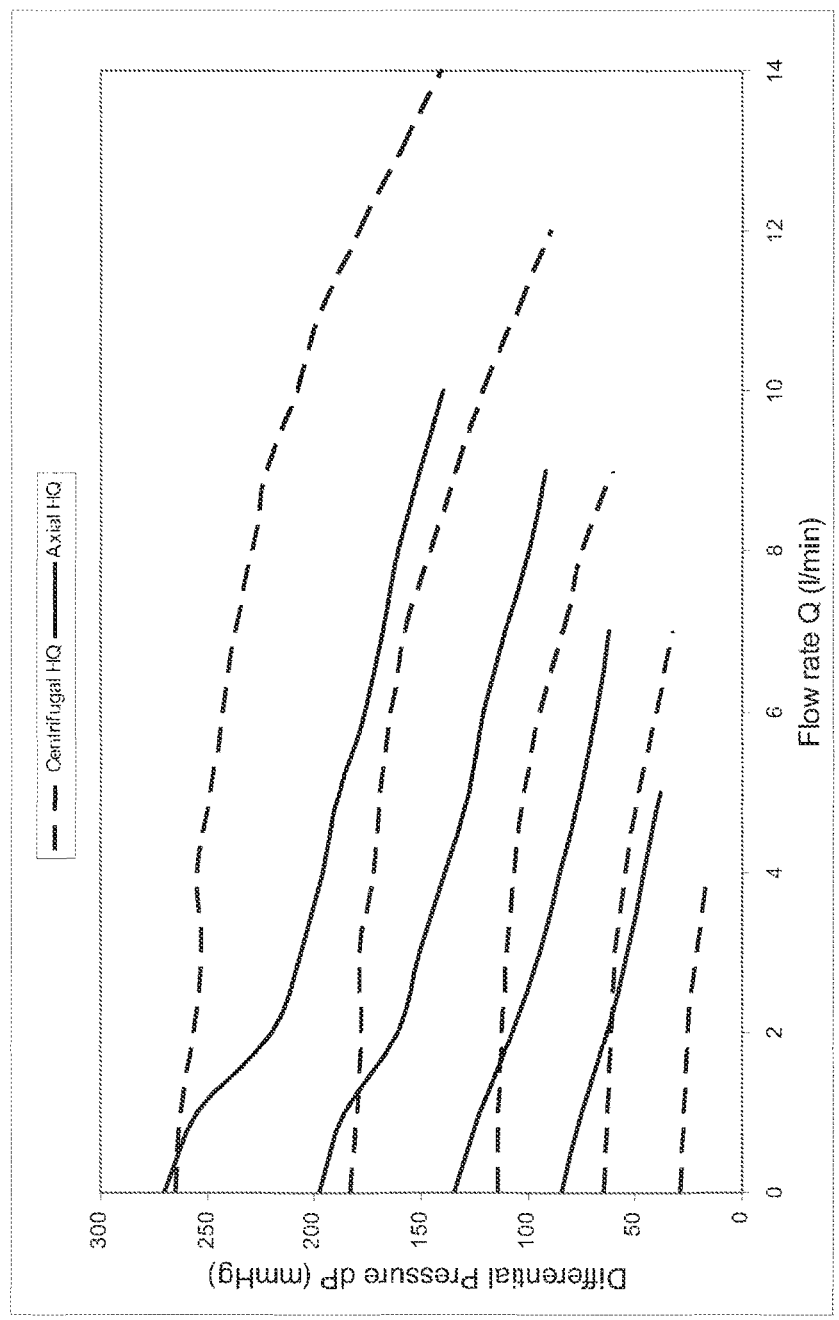
FIG. 3 is a chart illustrating both the characteristics of an axial flow pump and the characteristics of a centrifugal flow pump.

FIG. 3 shows both the native H-Q characteristics of the axial flow pump (solid lines) and the native H-Q characteristics of the centrifugal flow pump (broken lines). As illustrated in FIG. 3, the broken lines, representing the native H-Q characteristics of the centrifugal flow pump, tend to be "flatter" (i.e., closer to horizontal) than the solid lines, representing the native H-Q characteristics of the axial flow pump, indicating that the flow rate of the centrifugal flow pump is more responsive to changes in pressure differential. For the axial flow pump, a given change in pressure differential corresponds to a larger change in flow rate as compared to the centrifugal flow pump. Thus, each "type" of pump, whether an axial flow pump or a centrifugal flow pump, has its own set of H-Q curves that define its native H-Q characteristics. If a particular H-Q curve native to a first pump type (e.g., a centrifugal flow pump) is desired during the operation of a second pump type (e.g., an axial flow pump), then it could be achieved by changing speeds in the second pump type (axial flow pump) such that desired the H-Q curve of the first pump type can be simulated. For instance, one particular H-Q curve native to a centrifugal pump would intersect multiple H-Q curves (each representing different speeds) native to an axial flow pump when laid over a graph containing a series of H-Q curves. Therefore, to simulate the desired H-Q curve native to the centrifugal pump using the axial flow pump, the speed of the axial flow pump is modified and changed accordingly (i.e., at the points where the series of H-Q curves native to the axial flow pump intersect with the desired H-Q curve of the centrifugal pump). One motivation for this H-Q modification is to increase the responsiveness of the pump to the physiological need. It is believed that the need for perfusion is reflected in the differential pressure of the pump. By modifying the steepness of the pump's operational pressure-flow relationship, one can tune the flow change of the pump to be more responsive and thus better match patients' physiological needs.

The control system can use equations (1) and (2) to modify the operational H-Q characteristics of the axial flow pump to simulate the native H-Q characteristics of the centrifugal flow pump (or to simulate any desired H-Q characteristics). The control system can modify the operational H-Q characteristics of the axial flow pump by adjusting the speed of the axial flow pump as a function of given pump speed and flow rate.

The speed adjustments for modifying the operational H-Q characteristics of the axial flow pump to simulate characteristics of the centrifugal flow pump is represented in the following equation:

$$H=f_C(Q,S)=f_{AF}(Q,S+\Delta S) \tag{3}$$

In equation (3), S is the initial pump rotor speed and $S+\Delta S$ is the target pump rotor speed needed to simulate the characteristics of the centrifugal flow pump. Solving for $\Delta S$ from equation (3), we have $$\Delta S=f_S(Q,S) \tag{4}$$

Therefore, for any given set of (Q, S), if the control system varies the actual pump speed from the given pump speed S by an amount equal to $\Delta S=f_S(Q, S)$, the operational H-Q characteristics of the axial flow pump will match characteristics of a centrifugal flow pump.

Mathematically, this can be illustrated by substituting $\Delta S$, calculated from equation (4), into equation (3):

$$H=f_{AF}[Q,S+f_S(Q,S)] \tag{5}$$

where, for any given set of (Q, S), equation (5) gives the same value of H as equation (2). In other words, function $f_{AF}[Q, S+f_S(Q, S)]$ is the same as function $f_C(Q, S)$.

As stated above, function $H=f_C(Q, S)$ can be used to represent any desired pump characteristics. Therefore, the above method can be used to modify the operational characteristics of the axial flow pump to match any desired pump characteristics.

In equation (5), the set pump speed S (initial speed) is often already known, but the flow rate Q is to be determined. It is possible to use a flow sensor to measure the flow rate Q of the axial flow pump. However, a flow sensor potentially adds to the complexity, size and cost of the ventricular assist device, and also adds complexity to the surgical procedure for implanting the ventricular assist device (if the sensor is not integrated into the pump or into the inflow and/or outflow conduit). Flow sensors that can be implanted with the pump and used for the purpose of measuring flow (or pressure) can be used as an alternative, but add cost. Sensors also introduce an added level of complexity and an extra concern for purpose of reliability. Until sensors are less cost prohibitive and when they become more practical for this purpose, the flow rate Q is estimated without the use of a flow meter. U.S. Pat. No. 6,991,595, which is incorporated herein by reference, discloses a method for estimating the flow rate Q from the pump speed (or motor speed) and pump power consumption PC or from the pump speed (or motor speed) and the current I of the electric motor. Assuming pump power consumption PC is used to calculate the flow rate Q, we have $$Q=f_Q(S,PC) \tag{6}$$

As a result, the speed adjustment $\Delta S$ can be expressed as a function of pump speed S and pump power consumption PC by substituting equation (6) into equation (4):

$$\Delta S=f_S(Q,S)=f_S(f_Q(S,PC),S) \tag{7}$$

Then, in order to modify the operational H-Q characteristics of the axial flow pump to match desired characteristics, the control system adjusts the set pump speed by an amount $\Delta S$ that is a function of pump speed and power consumption, both of which can be obtained from the control system without any external sensors.

The following is an example illustrating how $\Delta S$ is calculated using simple, low order polynomials. In this example, the native H-Q characteristics of an axial flow pump are approximated by an equation:

$$H = aQ + b \tag{8}$$

where each of a and b is a function of pump speed S $$a = \alpha S + \beta \tag{9}$$

$$b = \gamma S^2 + \delta S + \epsilon \tag{10}$$

where $a$, $\beta$, $\gamma$, $\delta$ and $\epsilon$ are constants.

The desired H-Q characteristics (also referred to as target H-Q characteristics) are different than the native H-Q characteristics. In this example, the desired H-Q characteristic for the axial flow pump is a straight line and is expressed as:

$$H = mQ + n \tag{11}$$

where m and n can also be functions of the pump S and can be expressed as:

$$m = f_m(S) \tag{12}$$

$$n = f_n(S) \tag{13}$$

Similar to equation (3), to modify the operational characteristics of the axial flow pump to simulate the desired characteristics of equation (11), the speed of the axial flow pump can be varied from an initial rotor speeds by a certain amount $\Delta S$, and the following equation is to be satisfied:

$$H = aQ + b = mQ + n$$

$$H = [\alpha(S+\Delta S) + \beta]Q + [\gamma(S+\Delta S)^2 + \delta(S+\Delta S) + \epsilon] = mQ + n \tag{14}$$

On the left side of the equation is $aQ+B$ representing the native H-Q characteristics of the pump. On the right side of the equation is $mQ+n$ representing the desired or target H-Q characteristics. In Equation 14, the expressions in Equations (9) and (10) have been used for a and b, and $S+\Delta S$ representing the target pump rotor speed has been inserted in place of the starting pump rotor speed S.

Solving for $\Delta S$ from equation (14), we have $$\Delta S = -S + \frac{-(aQ+\delta) \pm \sqrt{(aQ+\delta)^2 - 4\gamma(\beta Q + \varepsilon - mQ - n)}}{2\gamma} \tag{15}$$

Since pump speed $(S+\sim S)$ cannot be negative, the positive square root is used:

$$\Delta S = -S + \frac{-(aQ+\delta) + \sqrt{(aQ+\delta)^2 - 4\gamma(\beta Q + \varepsilon - mQ - n)}}{2\gamma} \tag{16}$$

Taking into consideration that m and n can also be functions of pump speed S, equation (16) can be expressed as:

$$\Delta S = -S + \frac{-(aQ+\delta) + \sqrt{(aQ+\delta)^2 - 4\gamma[\beta Q + \varepsilon - f_m(S)Q - f_n(S)]}}{2\gamma} \tag{17}$$

where the flow rate Q of the axial flow pump can be estimated from the pump speed (or motor speed) and pump power consumption or from the pump speed (or motor speed) and the current of the electric motor. From the foregoing, it can be understood that the speed adjustment $\Delta S$ needed to simulate the desired H-Q characteristics is a function of flow rate Q and the starting rotor speed S (see Equation 17), and the function is derived from or based on the native H-Q characteristics of the pump and the desired H-Q characteristics (see Equation 14). The native H-Q characteristics of the pump and the desired H-Q characteristics can be stored in the effective memory of the control system 20, such as in memory 28.

When the control system adjusts the pump speed by an amount equal to $\Delta S$ as set forth in equation (17), the operational characteristics of the axial flow pump will be modified to simulate the desired characteristics of equation (11). Stated differently, if S is replaced by $S+\Delta S$ in equation (8), the H-Q characteristics of the axial flow pump as described by equation (8) will be modified to simulate the desired H-Q characteristics described by equation (11).

Figure 4:
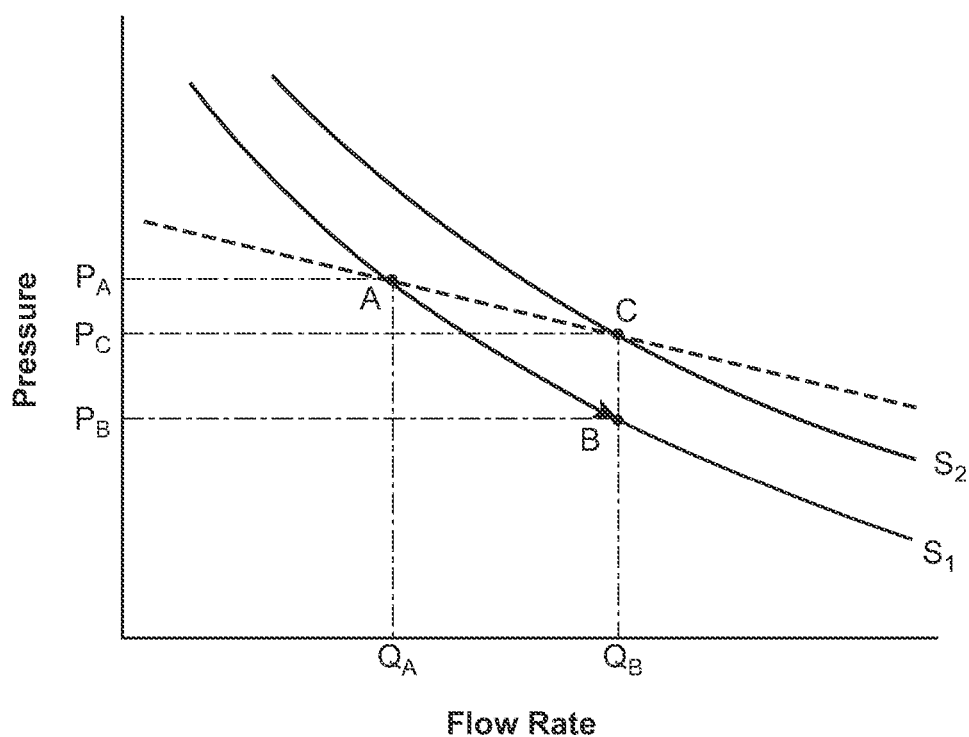
FIG. 4 is a chart illustrating an example of how the characteristics of an axial flow pump are modified to achieve desired pump characteristics.

FIG. 4 graphically illustrates how the adjustment of pump rotor speed S of the pump is accomplished at a particular point on the pump map to modify the characteristics of the axial flow pump as set forth in equations (8), (9) and (10) to simulate the desired H-Q characteristics of equation (11).

In FIG. 4, the native H-Q characteristics of the pump are represented by the H-Q curves illustrated in solid line, each H-Q curve corresponding to a single pump rotor speed that differs from that of the other H-Q curve. Only two H-Q curves (two rotor speeds) are illustrated for clarity and ease of illustration of this example, and it is to be understood that the native H-Q characteristics of the pump actually include more H-Q curves, there being one H-Q curve for every pump rotor speeds at which the pump can possibly be operated. The desired H-Q curve (also referred as the target H-Q curve) is illustrated in broken line. The desired H-Q curve is not native of the pump (i.e., is different from the pump's native H-Q curves) and does not correspond to a single pump rotor speed.

Referring to FIG. 4, the pump initially operates at point A with speed S1. From the estimated flow rate $Q_A$, the pressure $P_A$ can be calculated using the following equation:

$$P_A = aQ_A + b \tag{18}$$

When there is a change in pump pressure and the flow rate changes to a new value QB, the operating point of the axial flow pump would change from A to B as shown in FIG. 4, if there is no rotor speed adjustment $\Delta S$. In moving from A to B, the pump is operating along one of the solid lines representing its native H-Q characteristics. Thus, without a rotor speed adjustment $\Delta S$, the operational H-Q characteristic of the pump correspond to its native H-Q characteristics. In order to modify the operational H-Q characteristics of the axial flow pump to simulate the desired characteristics of the flatter broken line, the pump rotor speed is changed to bring the pump's operating point to C. Operating point C corresponds to the new flow rate value $Q_B$ on the desired H-Q curve (broken line). The following describes how the new pump rotor speed can be determined.

At point C, the desired pressure can be calculated from the following equation:

$$P_C = mQ_B + n \tag{19}$$

To modify the characteristics of the axial flow pump as described by equation (18) to simulate the desired characteristics of equation (19), the following equation is to be satisfied:

$$H = aQ_B + b = (\alpha S_2 + \beta)Q_B + (\gamma S_2^2 + \delta S_2 + \epsilon) = mQ_B + n \qquad (20)$$

where $S_2$ is the desired pump speed and is the sum of starting pump speed S and speed adjustment $\Delta S$.

Solving for $S_2$ from equation (20), we have $$S_2 = \frac{-(\alpha Q_B + \delta) \pm \sqrt{(\alpha Q_B + \delta)^2 - 4\gamma(\beta Q_B + \epsilon - mQ_B - n)}}{2\gamma} \qquad (21)$$

Since pump speed $S_2$ cannot be negative, the positive square root is used to obtain:

$$S_2 = \frac{-(\alpha Q_B + \delta) + \sqrt{(\alpha Q_B + \delta)^2 - 4\gamma(\beta Q_B + \epsilon - mQ_B - n)}}{2\gamma} \qquad (22)$$

By operating the pump at the new pump speed $S_2$ as a function of flow rate QB according to equation (22), the characteristics of the axial flow pump as set forth by equation (18) is modified to simulate the desired characteristics of equation (19).

The method described by equations (18) to (22) has been successfully implemented on a test bench using an axial flow pump and a centrifugal flow pump. In the test, the operational characteristics of the axial flow pump were modified to simulate the characteristics of the centrifugal pump.

From the forgoing description, it can be understood that the step of modifying the H-Q characteristics of the pump can include adjusting the rotor speed S by an amount $\Delta S$, from an initial speed to a target speed, such that the operating point of the pump on a graph of pressure differential versus flow rate (e.g., FIG. 4) moves from an initial point (e.g., Point B in FIG. 4) to a target point (e.g., Point C in FIG. 4). The initial and target points have the same flow rate values (e.g., $Q_B$ in FIG. 4) and different pressure differential values (e.g., $P_B$ and $P_C$ in FIG. 4). From the below description of set response time, it can be understood that the speed adjustment can be repeated any number of times. When the speed adjustment is repeated multiple times, the operating point of the pump moves to additional target points all of which lie on the same desired H-Q curve (e.g., broken line in FIG. 4). Therefore, modifying operational pressure-flow characteristics of a pump to simulate target pressure-flow characteristics can be performed by repeatedly adjusting the speed of the motor, from an initial speed to a target speed. With each repetition there is a new target speed. All the target speeds correspond to pump operation points on the same desired H-Q curve.

Figure 5:
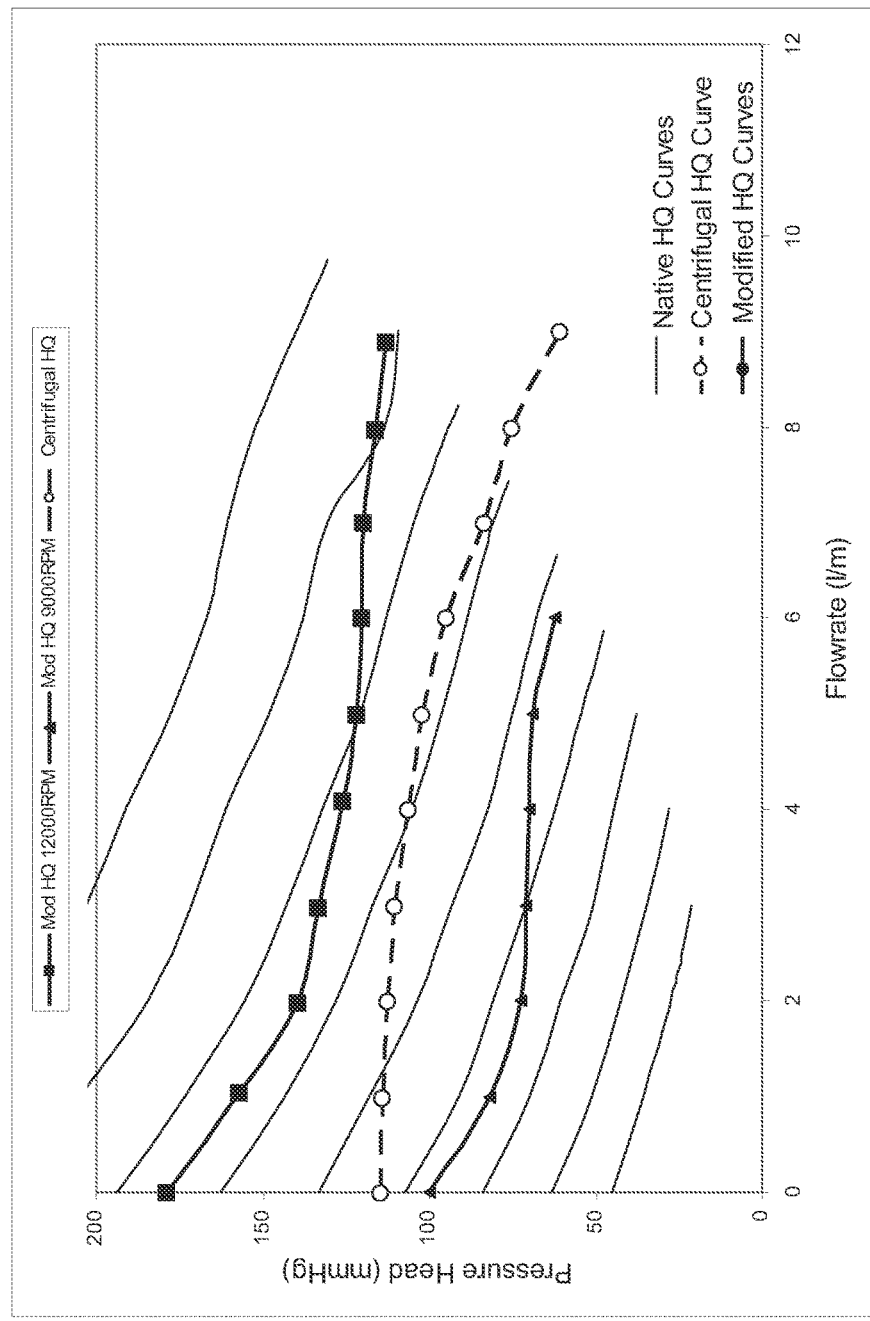
FIG. 5 is a chart illustrating the modified characteristics of an axial flow pump of a ventricular assist device.

FIG. 5 shows the native H-Q curves of the axial flow pump (solid lines without data markers) that correspond to pump speeds ranging from about 6,000 RPM to about 15,000 RPM by an increment of about 1,000 RPM. FIG. 5 also shows the native H-Q curve of the centrifugal pump (broken line) at the pump speed of about 4,000 RPM. As shown in FIG. 5, the H-Q curve of the centrifugal pump is "flatter" (i.e., closer to horizontal) than the H-Q curves of the axial flow pump, indicating that the change to the pressure differential of the centrifugal pump has more impact on its flow rate than the change to the pressure differential of the axial flow pump on its flow rate.

FIG. 5 further shows the modified H-Q curves of an axial flow pump (solid lines with data markers) that simulates the native H-Q characteristics of another pump with a different hydraulic design at the initial speed of 9,000 RPM and about 12,000 RPM. For this particular example, the axial flow pump starts at set initial speed. The desired H-Q curve for this test case is defined to be "flatter" than the native H-Q curves. Initially when the pressure differential across the pump changes, the flow responds by following the native H-Q curve corresponding to the initial rotor speed. At set response time (i.e., a time period after the pressure change), the method monitors and determines if the calculated pressure and flow falls on the desired H-Q curve. The response time can range from fraction of a second to many seconds, which results in high frequency response to cyclical variation or low frequency response to longer-term trends respectively. The response time need not correspond with the cardiac rhythm. For this test case, the response time is designed to make gradual low-frequency adjustment. The method calculates for and adjusts to the appropriate speed to achieve the desired pressure-flow relationship. The operating point of pump traverses from one point on the native H-Q curve at the initial speed to another point on the native H-Q curve at the calculated speed. The same process repeats itself for all levels of pressure change. The various pump operating points, resulting from multiple pressure changes, are all located on the desired H-Q curve. As FIG. 5 shows, the H-Q curves of the modified axial flow pump are "flatter," especially when the flow rate is greater than 2 liters/minute. This example demonstrates that the present invention is effective in modifying the characteristics of an axial flow pump so that the pump's flow rate is more responsive to pressure changes.

Every pump has a unique set of native H-Q curves defined at a range of operating speeds (or power or current). Accordingly, a target H-Q relationship not native to the pump type can be established by changing the speed of the pump to simulate the target pressure-flow curve desired. In the context of a blood pump, the pump becomes integrated into an individual's circulatory system. As the pressure across the pump inflow and pump outflow changes, so does the blood flowing out of the pump at a given speed. For instance, if the peripheral vascular resistance increases, the motor, at constant speed, is working harder to deliver blood against the vasculature, therefore, the flow decreases. The blood flow through the pump increases as the pressure differential decreases when the vascular resistance decreases.

From a different perspective, a particular pressure-flow characteristic can be a function of, or can be estimated from, power and/or current and voltage and rotor speed. For example, when there is an increase in peripheral vascular resistance, the outflow pressure is comparatively higher than the inflow pressure resulting in an increase in pressure differential across the blood pump. Consequently, less flow is delivered by the pump at constant speed leading to lower current (and lower power). The converse is also true. Therefore, the native H-Q curves for any pump type also correspond to different levels of power or current generating the respective different motor speeds.

Figure 6:
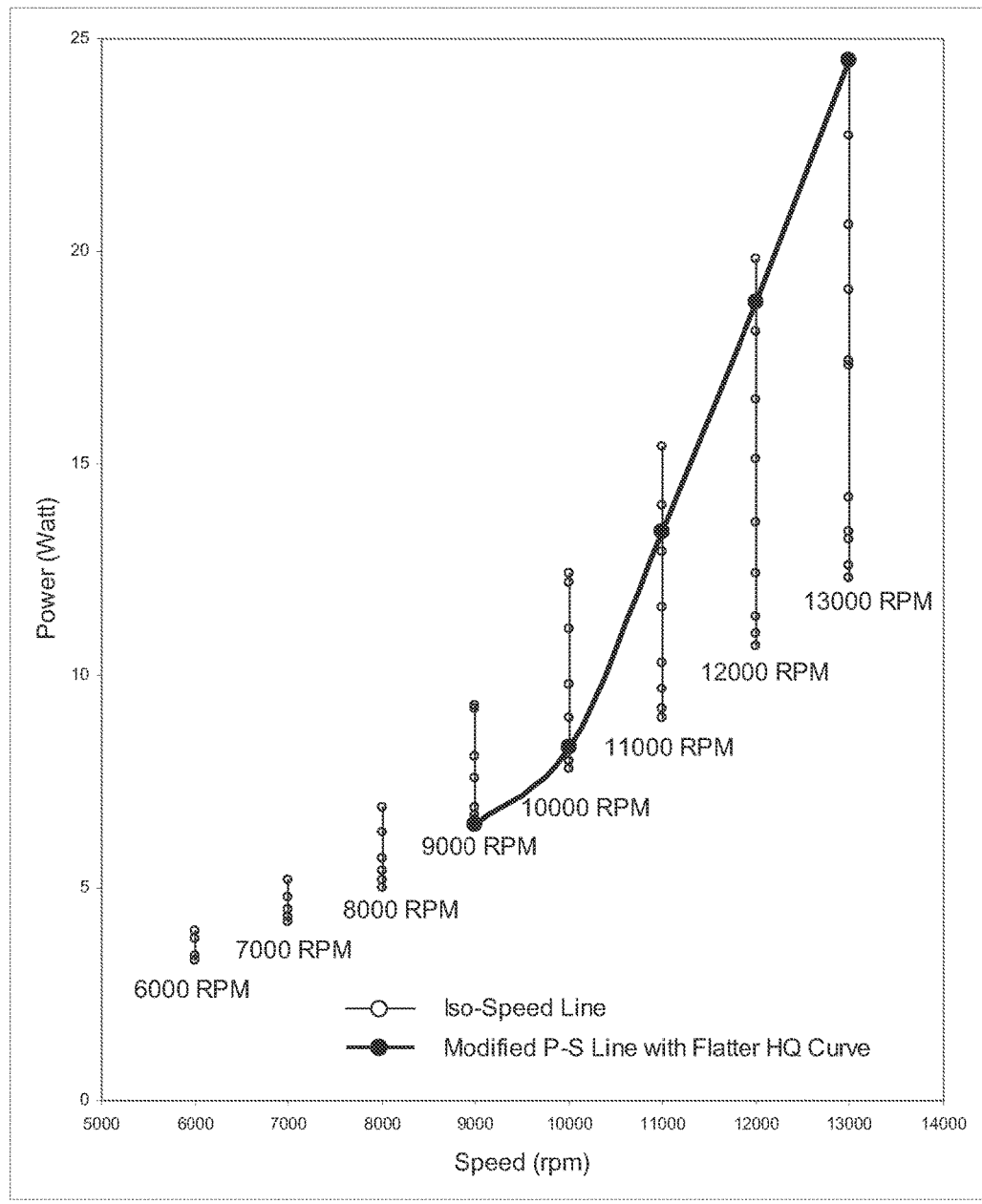
FIG. 6 is a chart illustrating characteristics of an axial flow pump of a ventricular assist device.

For a particular motor and pump, unique relations exist between the motor power (or current or voltage), flow, and differential pressure. As a result, controlling the pump's speed so that it follows a particular power-speed relation will alter the effective pressure-flow relation than would be achieved by forcing the pump to operate at a fixed speed. Thus, the control system can use a specified power-speed relation to modify the H-Q characteristics of the pump to simulate the desired H-Q characteristics of the centrifugal flow pump (or to simulate any desired H-Q characteristics). Using this approach the flow or pressure does not need to be explicitly estimated by the control system or measured. This approach can be understood by considering the pump's characteristics in the power-speed plane, as shown in FIG. 6. When a pump is set to a fixed speed, the pump will operate at power levels on a vertical line in this plane. As the pump power increases (as is generally the case with increasing flow) the operation point just moves vertically to a higher power but remains at the same speed. When the speed is changed the pump will operate on a different vertical line corresponding to the new speed. Thus in a fixed speed mode the pump operates on any one of a family of speed-power curves that are vertical lines illustrated as thin solid lines and labeled "IsoSpeed Line" in FIG. 6.

The control system can also force the pump to operate on a non-vertical curve in the power-speed plane. For example, if the selected curve is a line with a finite positive slope, as the power increases the controller will also increase the pump speed. One such curve, representative of a particular power-speed relation, is illustrated with a heavy solid line and labeled "Modified P-S Line" in FIG. 6. Thus the pump generally operates at a higher flow than the fixed speed control would allow. In effect this causes the pump to operate on a less steep curve in the H-Q plane, effectively modifying the operational H-Q characteristics of the pump. The pump can be controlled to operate along another non vertical curve (non-vertical power-speed relation) that differs from the one illustrated in FIG. 6. This manner of control, by adjusting the speed of the axial flow pump based only on the measured power and speed without estimating or measuring flow rate or pressure, can be used to produce more desirable H-Q characteristics of the axial flow pump.

From the foregoing description, it can be understood that a speed adjustment to simulate any desired H-Q characteristics can be a function of the starting or initial rotor speed and the power consumption of the motor. As described in connection with FIG. 4, the speed adjustment can be a function of the initial rotor speed and the flow rate of the 20 pump. Therefore, the present invention encompasses speed adjustment as a function of the initial rotor speed and of either one or both of flow rate of the pump and power consumption of the motor.

An aspect of the above-described control methods is to determine which H-Q curve from the family of native H-Q curves the pump should operate on. The native H-Q curve on which the pump operates is referred to as the "effective H-Q curve." One approach is to select a specific operating point and then operate on the H-Q curve that passes through that point. This can be accomplished by controlling the pump in a fixed speed mode (e.g., point A to B in FIG. 4) and followed by adjusting the pump speed to achieve the desired operating condition or point (e.g., point C in FIG. 4). Once the pump's operating point is selected, the pump can be controlled to follow the particular H-Q curve that passes through the desired operating point. The response time between each pump speed adjustment can vary from a fraction of a second to many seconds. Depending on the need of the patient, the method can decrease the response time to react to the cyclical change at high frequency or conversely increase the response time to react to the long-term trend. The goal is to meet the perfusion need of the patient and loading 5 of the heart which manifests itself in the change in differential pressure across the pump.

For example, when a patient exercises, the left ventricular pressure increases which leads to decrease in the pressure differential across the pump. The method provides an operational flow-pressure relationship (that is different from the native relationship) to meet the physiological need.

From a safety standpoint, to avoid putting users or patients in danger resulting from any issue arises with the pump or physiologic conditions, upper and lower speed limits are preset to prevent the controller from driving the pump to undesirable speeds or conditions. Specifically, the pump speed will not be allowed to vary outside of a pre-specified acceptable operating window. In practice, floor and ceiling speeds are established to control loading and unloading of the heart as safety limits to avoids situations where the pump is pumping out too little or too much blood. When the speed is too low the pump may not be pumping out sufficient blood from the heart to support the patient. When the speed is too high, the pump may pump more blood out of the ventricle (if attached to the ventricle) than the rate at which blood fills the ventricle from the atrium, thus potentially causing collapse in the ventricle. It should be noted that the safety limits are individually specific for each person and the limits are set according to speed. In other words, the pump is allowed to operate anywhere on a number of H-Q curves, each defined by the speed of the pump, but not on the H-Q curves representing speeds beyond the floor or ceiling.

Any of the above methods may be implemented using computer program languages such as, for example, ActiveX, Java, C, and the C++ language and utilize object oriented programming methodology. Any such resulting program, having computer-readable code, may be embodied or provided within one or more computer readable storage media, thereby making a computer program product (i.e., an article of manufacture). The computer readable storage media may be, for instance, a fixed (hard) drive, diskette, optical disk, magnetic tape, semiconductor memory such as read-only memory (ROM), etc., or any transmitting/receiving medium such as the Internet or other communication network or link. The article of manufacture containing the computer code may be made and/or used by executing the code directly from one medium, by copying the code from one medium to another medium, or by transmitting the code over a network. For example, the computer code may be stored in the effective storage medium of the control system 20. The effective memory can be contained in the control system 20 (e.g., memory 28 in FIG. 1) or located remotely from the control system 20. When the effective memory is located remotely from control system 20, the computer code or fragments thereof can be transmitted from the effective memory to the control 10 system 20.

As shown in FIG. 7, the computer-readable code, which is embodied in the computer-readable storage media, computer program product or an article of manufacture, can have instructions for carrying out steps of the following exemplary method:

Modifying pressure-flow characteristics of a continuous flow pump (e.g., an axial flow pump) to simulate a particular set of pressure-flow characteristics (e.g., a centrifugal flow pump.)

The step of modifying the pressure-flow characteristics of the continuous flow pump can include one or more of the following sub-steps:

Sub-step 1: estimating a flow rate of the continuous flow pump from the speed of an electric motor and from the current or power consumption of the electric motor, wherein the electric motor drives the continuous flow pump; and Sub-step 2: adjusting the speed of the electric motor as a function of an estimated flow rate of the pump (e.g., the axial flow pump) and a set speed of the electric motor to simulate the desired pressure-flow characteristics (e.g., the centrifugal flow pump), wherein the function can be derived from the pressure-flow characteristics of the pump (e.g., the axial flow pump) and the desired pressure-flow characteristics (e.g., the centrifugal flow pump).

Figure 8:
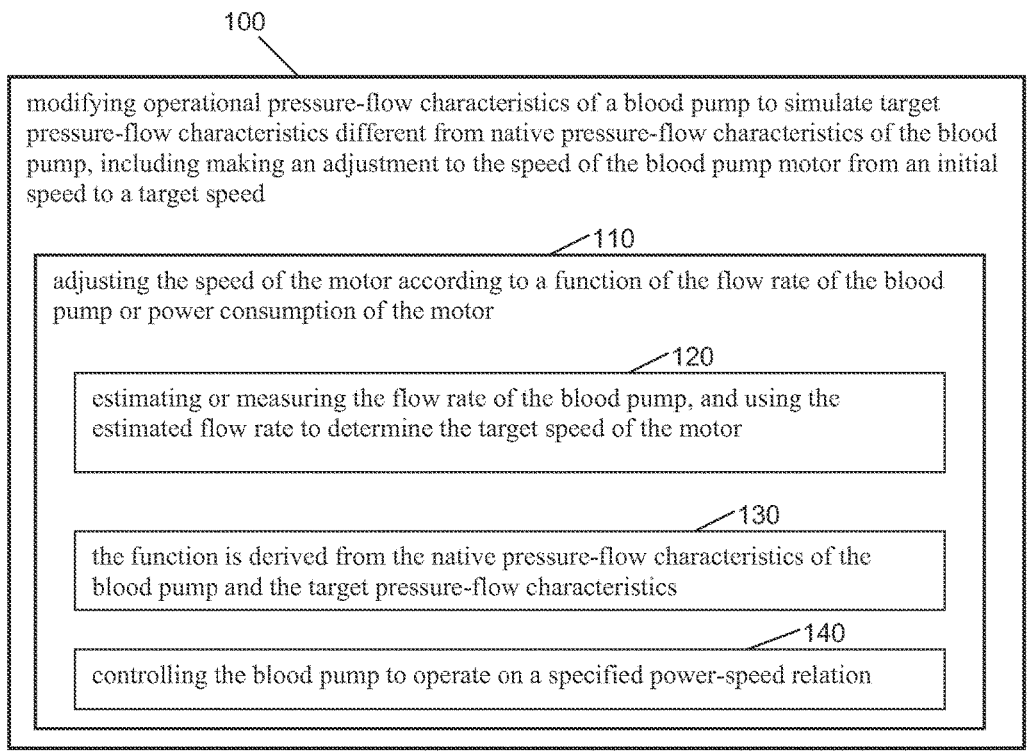
FIG. 8 is a chart showing computer instructions for carrying out the a step of an exemplary method of the invention.

As shown in FIG. 8, the computer-readable code, which is embodied in the computer-readable storage media, computer program product or an article of manufacture, can have instructions for carrying out steps of the following exemplary method.

Box 100 represents instructions for carrying out the step of modifying operational pressure-flow characteristics of a blood pump to simulate target pressure-flow 5 characteristics different from native pressure-flow characteristics of the blood pump, including making an adjustment to the speed of a blood pump motor from an initial speed to a target speed.

In FIG. 8, a smaller box contained within a larger box represents an optional sub-step for performing the step represented by the larger box. Box 110 represents instructions for adjusting the speed of the motor according to a function of the flow rate of the blood pump or of the power consumption of the motor. Box 120 represents instructions for estimating or measuring the flow rate of the blood pump, and using the estimated flow rate to determine the target speed of the motor. Box 130 represents instructions for adjusting the speed of the motor according to a function is derived from the native pressure-flow characteristics of the blood pump and the target pressure-flow characteristics. Box 140 represents instructions for adjusting the speed of the motor by controlling the blood pump to operate on a specified power-speed relation.

Although the above describes certain ventricular assist devices of the present invention, the present invention is not limited to ventricular assist devices. In fact, the 20 present invention may be used with any fluid delivery system. Additionally, the present invention is not limited to axial flow pumps. The present invention may be used to modify the performance of any suitable pump, including any displacement pump such as a gear pump or a reciprocating-type pump or any velocity pump such as a radial flow pump, a centrifugal flow pump, or a mixed flow pump. Furthermore, the present invention can be used to modify the performance of a pump to match any desired pump characteristics. For example, the present invention can be used to modify the performance of a pump so that the flow rate of the pump is less responsive to changes in the pump pressure, as well as more responsive to changes in pump pressure.

While particular embodiments of the present invention have been shown and 30 described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A blood pump system for providing ventricular assistance to a patient, the blood pump system comprising:
a continuous flow blood pump;
a motor drivingly coupled with the continuous flow blood pump; and
a control unit operatively coupled with the motor, the control unit including a processor and memory storing (a) target pump characteristic data defining a target pressure-flow curve for the continuous flow blood pump, the target pressure-flow curve being different from a pressure-flow characteristics curve of the continuous flow blood pump when driven by the motor at a constant rotational rate, and (b) instructions that when executed by the processor cause the processor to:
operate the motor at a first rotational rate;
determine a first flow rate of the continuous flow blood pump driven by the motor at the first rotational rate;
determine a second rotational rate for the motor as a function of the first rotational rate and the first flow rate via accessing the target pump characteristic data, the second rotational rate being different from the first rotational rate and selected to cause the continuous flow blood pump to generate a resulting pressure differential and a resulting flow rate in conformance with the target pressure-flow curve; and
operate the motor at the second rotational rate.

2. The blood pump system of claim 1, wherein the instructions, when executed by the processor, further cause the processor to estimate the first flow rate based on the first rotational rate and a current or power consumption of the motor.

3. The blood pump system of claim 1, wherein the instructions, when executed by the processor, cause the processor to estimate a pressure differential across the blood pump based on the first rotational rate and a current or power consumption of the motor and use the estimated pressure differential in the determination of the second rotational rate.

4. The blood pump system of claim 1, wherein the target pump characteristic data includes a specified power-speed relationship.

5. The blood pump system of claim 4, wherein the target pump characteristic data includes a plurality of different power-speed relationships, each of the power-speed relationships corresponding to a respective operational level for the blood pump.

6. The blood pump system of claim 1, wherein the target pump characteristic data defines a target pressure differential across the pump as a function of flow rate through the blood pump.

7. The blood pump system of claim 1, wherein the target pump characteristic data includes data corresponding to a plurality of different operational levels of the blood pump, each of the different operational levels of the blood pump producing a different differential pressure across the blood pump for a reference flow rate through the blood pump.

8. The blood pump system of claim 1, wherein the instructions, when executed by the processor, cause the processor to:
determine a second flow rate of the continuous flow blood pump driven by the motor at the second rotational rate;
determine a third rotational rate for the motor as a function of the second rotational rate and the second flow rate via accessing the target pump characteristic data, the third rotational rate being different from each of the first and second rotational rates and selected to cause the continuous flow blood pump to generate a second resulting pressure differential and a second resulting flow rate in conformance with the target pressure-flow curve; and
operate the motor at the third rotational rate.

9. The blood pump system of claim 1, wherein the continuous flow blood pump comprises an axial flow pump, a centrifugal pump, or a mixed flow pump.

10. A method for controlling a continuous flow blood pump driven by a motor, the method comprising:
operating the motor at a first rotational rate;
measuring and/or estimating a first flow rate of the continuous flow blood pump driven by the motor at the first rotational rate;

determining a second rotational rate for the motor as a function of the first rotational rate and the first flow rate via accessing target pump characteristic data stored in a memory device, the target pump characteristic data defining a target pressure-flow curve for the continuous flow blood pump, the target pressure-flow curve being different from a pressure-flow curve of the continuous flow blood pump when driven by the motor at a constant rotational rate, the second rotational rate being different from the first rotational rate and selected to cause the continuous flow blood pump to generate a resulting pressure differential and a resulting flow rate in conformance with the target pressure-flow curve; and operating the motor at the second rotational rate.

11. The method of claim 10, wherein the first flow rate is estimated based on the first rotational rate and a current or power consumption of the motor.

12. The method of claim 10, wherein the first flow rate is measured.

13. The method of claim 10, wherein determining the second rotational rate includes estimating a pressure differential across the blood pump based on the first rotational rate and a current or power consumption of the motor.

14. The method of claim 10, wherein determining the second rotational rate includes measuring a pressure difference across the blood pump.

15. The method of claim 10, wherein the target pump characteristic data includes a specified power-speed relationship.

16. The method of claim 15, wherein the target pump characteristic data includes a plurality of different power-speed relationships, each of the power-speed relationships corresponding to a respective operational level for the blood pump.

17. The method of claim 10, wherein the target pump characteristic data defines a target pressure differential across the pump as a function of flow rate through the blood pump.

18. The method of claim 10, wherein the target pump characteristic data includes data corresponding to a plurality of different operational levels of the blood pump, each of the different operational levels of the blood pump producing a different differential pressure across the blood pump for a reference flow rate through the blood pump.

19. The method of claim 10, comprising:
measuring and/or estimating a second flow rate of the continuous flow blood pump driven by the motor at the second rotational rate;
determining a third rotational rate for the motor as a function of the second rotational rate and the second flow rate via accessing the target pump characteristic data stored in the memory device, the third rotational rate being different from each of the first and second rotational rates and selected to cause the continuous flow blood pump to generate a second resulting pressure differential and a second resulting flow rate in conformance with the target pressure-flow curve; and
operating the motor at the third rotational rate.

20. The method of claim 10, wherein the continuous flow blood pump comprises an axial flow pump, a centrifugal pump, or a mixed flow pump.

* * * * *